(12) United States Patent
Ortiz

(10) Patent No.: US 7,645,287 B2
(45) Date of Patent: *Jan. 12, 2010

(54) ARTICULATING ANASTOMOTIC RING APPLIER

(75) Inventor: Mark S. Ortiz, Milford, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 459 days.

This patent is subject to a terminal disclaimer.

(21) Appl. No.: 11/121,345

(22) Filed: May 3, 2005

(65) Prior Publication Data
US 2006/0253138 A1    Nov. 9, 2006

(51) Int. Cl.
*A61B 17/08* (2006.01)
*A61B 17/10* (2006.01)

(52) U.S. Cl. .................................................... 606/153
(58) Field of Classification Search ............. 600/141, 600/146–149, 201, 207; 606/139–141, 151, 606/157, 198, 153; 623/1.11, 1.12; 604/528, 604/104–113
See application file for complete search history.

(56) References Cited

U.S. PATENT DOCUMENTS

| | | | | |
|---|---|---|---|---|
| 5,282,810 | A * | 2/1994 | Allen et al. | 606/150 |
| 5,669,918 | A * | 9/1997 | Balazs et al. | 606/139 |
| 5,855,312 | A |   1/1999 | Toledano | |
| 6,033,378 | A * | 3/2000 | Lundquist et al. | 604/95.01 |
| 6,171,321 | B1 |   1/2001 | Gifford et al. | |
| 6,451,029 | B1 |   9/2002 | Yeatman | |
| 6,485,496 | B1 * | 11/2002 | Suyker et al. | 606/153 |
| 7,309,341 | B2 * | 12/2007 | Ortiz et al. | 606/153 |
| 2003/0032967 | A1 | 2/2003 | Park et al. | |
| 2004/0176751 | A1 | 9/2004 | Weitzner et al. | |
| 2005/0049614 | A1 | 3/2005 | Cendan | |
| 2005/0070934 | A1 * | 3/2005 | Tanaka et al. | 606/153 |
| 2005/0070939 | A1 * | 3/2005 | Beaupre | 606/154 |

FOREIGN PATENT DOCUMENTS

| DE | 43 32 238 | 12/1994 |
|---|---|---|
| EP | 1520531 | 4/2005 |

OTHER PUBLICATIONS

Office Action dated Jan. 4, 2006, for U.S. Appl. No. 10/675,497, filed Sep. 30, 2003.
European Search Report, dated Sep. 13, 2006, for EP Application No. 06252324.6.

* cited by examiner

*Primary Examiner*—(Jackie) Tan-Uyen T Ho
*Assistant Examiner*—Dianne Dornbusch
(74) *Attorney, Agent, or Firm*—Dean Garner

(57) ABSTRACT

A surgical instrument for applying an anastomotic ring device comprises a handle connected to an anastomotic ring deployment mechanism by a shaft. The shaft has at least one articulation joint that is capable of articulating in at least one direction to allow the surgeon to alter the angle of approach in order to compensate for disadvantageous placement of a trocar port through which the instrument is inserted. An articulation joint may comprise a ribbed member. One or more cables may be used to effect articulation of the articulation joint.

8 Claims, 13 Drawing Sheets

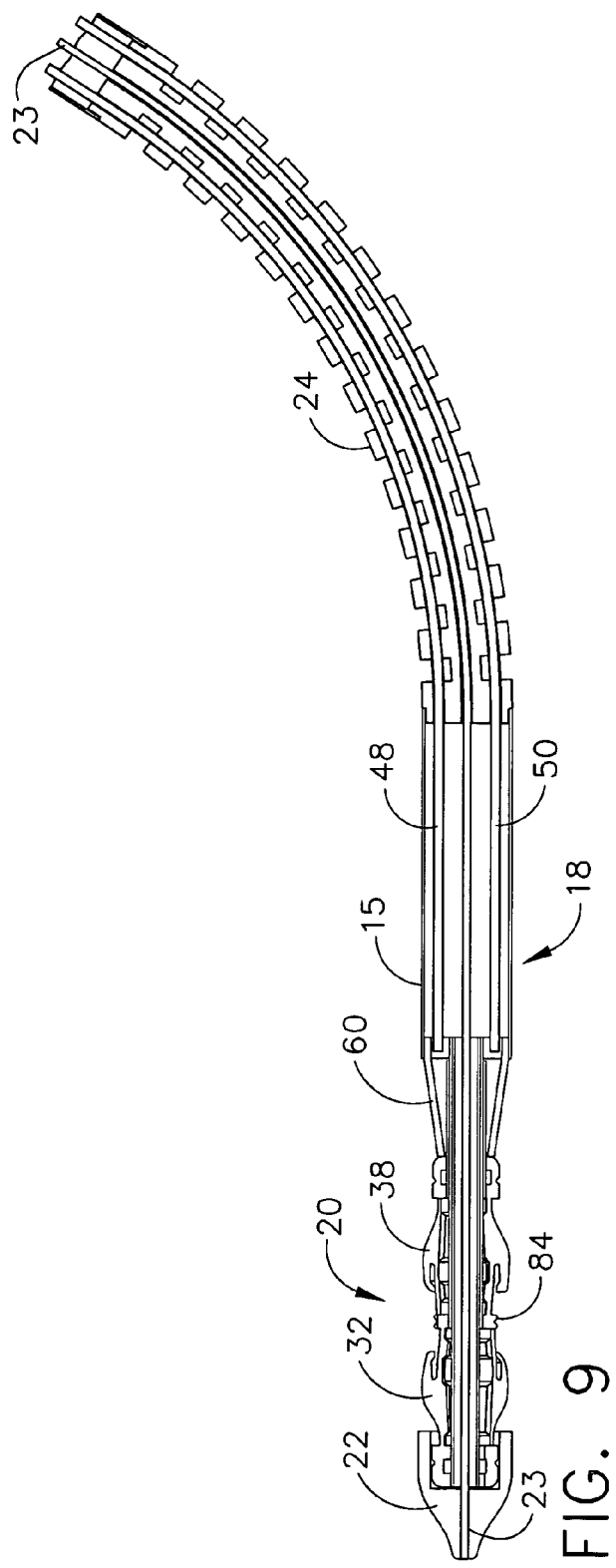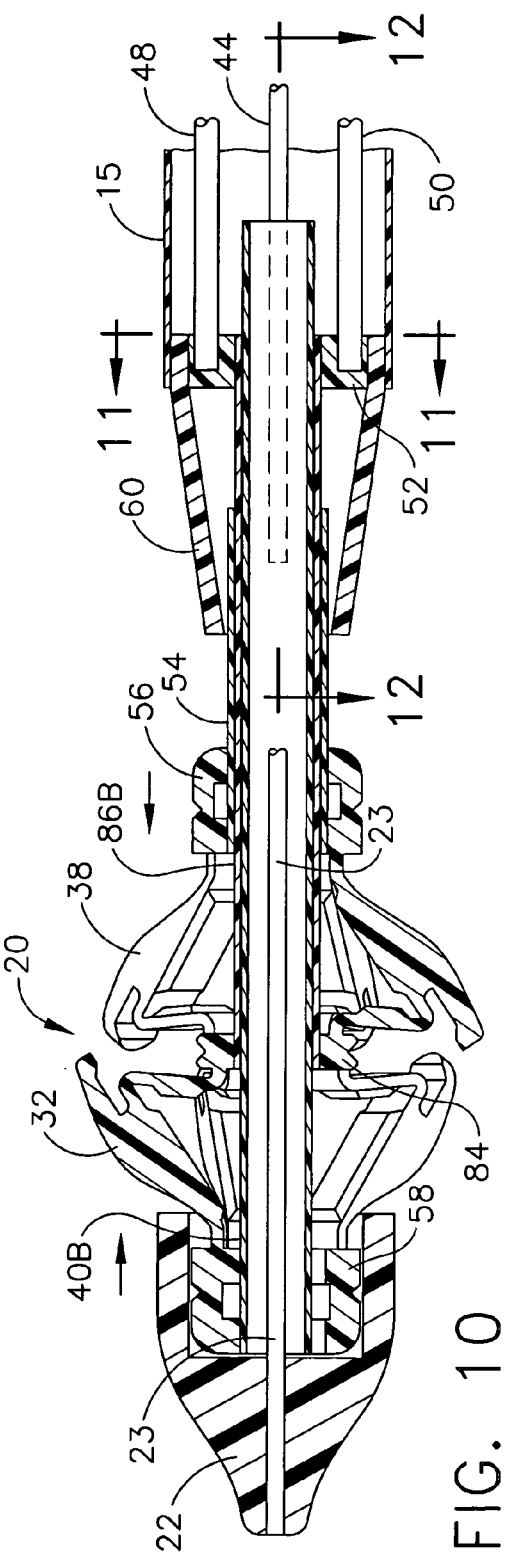

ARTICULATING ANASTOMOTIC RING APPLIER

FIELD OF THE INVENTION

The present invention relates, in general, to surgery and, more particularly, to a device for performing a surgical procedure on the digestive system.

BACKGROUND OF THE INVENTION

The percentage of the world population suffering from morbid obesity is steadily increasing. Severely obese persons may be susceptible to increased risk of heart disease, stroke, diabetes, pulmonary disease, and accidents. Because of the effects of morbid obesity on the life of the patient, methods of treating morbid obesity have been the subject of intense research.

One known method for treating morbid obesity includes the use of anastomotic rings. Devices for applying anastomotic rings are known in the art. Devices of this nature are commonly adapted to insert a compressed anastomotic ring to an anastomotic opening formed between proximate gastrointestinal tissue walls. These applier devices may utilize a ring deployment mechanism comprising an expansion element that is actuated once the compressed ring is placed in the anastomotic opening, causing the anastomotic ring to expand from its compressed, cylindrically-shaped position to an actuated, hollow rivet-shaped position.

However, the devices known in the art commonly comprise a rigid shaft attached to a handle. While these devices may be well-adapted to deploy the ring, it may be difficult to properly deploy the ring when the trocar port has been improperly placed, as the surgeon may be unable to find a workable angle of approach. This may require the surgeon to remove and reposition the trocar, thereby lengthening the time of the surgery. Alternatively, the surgeon may attempt to place and deploy the ring in spite of the difficult angle of approach. This may cause the ring to be incorrectly deployed, leading to complications or failure of the anastomosis.

Consequently, it may be desirable to have an applier that allows the surgeon to alter the angle of approach at the anastomosis site, such as at the gastrojejunum and the jejunum, when the trocar ports have been improperly placed.

BRIEF SUMMARY OF THE INVENTION

Embodiments of the invention provide an anastomotic ring applier device that is capable of articulation, thereby allowing a surgeon to improve the angle of approach of the applier after insertion through a trocar port. Embodiments may also allow for improved viewing of the anastomosis with a laparoscope by providing for articulation of the applier device.

In one embodiment, a surgical instrument for applying an anastomotic ring device is provided, comprising a handle connected to a ring deployment mechanism by an elongated shaft. The shaft is adapted to communicate an actuating force to the ring deployment mechanism. The shaft also comprises at least one flexible joint that is adapted to allow the elongated shaft to articulate. In this manner, the surgeon may articulate the shaft in order to alter the angle of approach of the ring deployment mechanism and/or to allow an improved view of the anastomosis through a laparoscope.

In another embodiment, an instrument comprises a handle connected to a ring deployment mechanism by an elongated shaft. The shaft comprises at least one flexible joint that is adapted to articulate via a push/pull cable. This embodiment also allows the surgeon to alter the angle of approach of the ring deployment mechanism and/or to view the anastomosis through a laparoscope.

In yet another embodiment, an instrument comprises a handle connected to an actuating member for deploying an anastomotic ring from a cylindrical, unactuated position to an actuated, hollow rivet-forming shape in response to a compressive actuating force. The handle includes a mechanism for producing the compressive actuating force. The instrument further comprises an elongated shaft to connect the handle to the actuating member. The shaft is adapted to transfer the compressive actuating force. The shaft further comprises at least one flexible joint adapted to allow the shaft to articulate. In this embodiment, the surgeon may articulate the shaft in order to more accurately place the actuating member to apply the compressive actuating force to deploy the anastomotic ring to the actuated, hollow rivet-forming position and/or may also obtain an improved view of the anastomosis with a laparoscope by articulating the elongated shaft.

BRIEF DESCRIPTION OF THE FIGURES

The accompanying drawings, which are incorporated in and constitute a part of this specification, illustrate versions of the invention, and, together with the general description of the invention given above, and the detailed description of the versions given below, serve to explain the principles of the present invention.

FIG. 9 is a cross-sectional view of a distal portion of the device of FIG. 1.

FIG. 10 is a cross-sectional view of the anastomotic ring deployment mechanism of the device of FIG. 1 in the actuated position.

DETAILED DESCRIPTION OF EMBODIMENTS OF THE INVENTION

Figure 1:
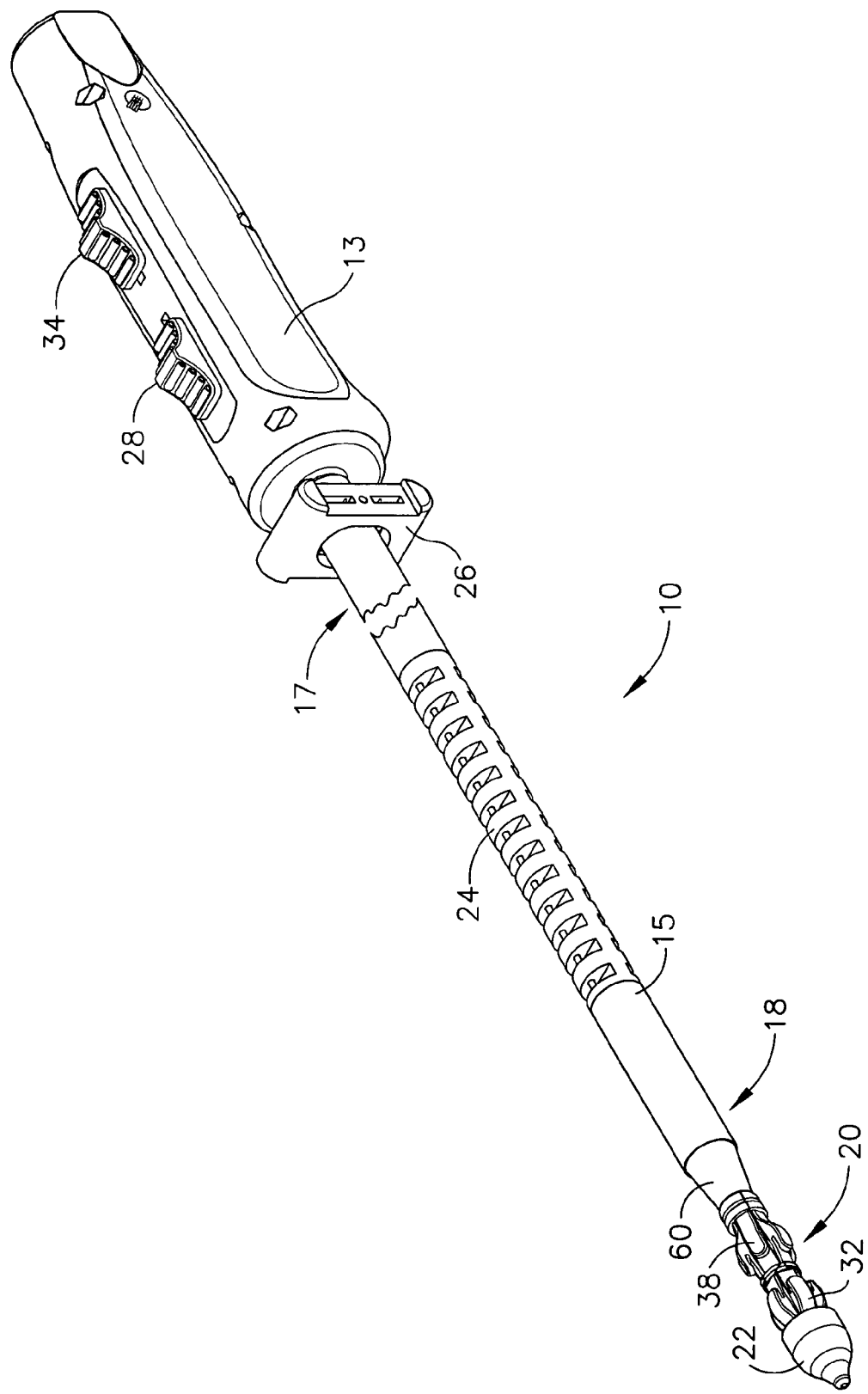
FIG. 1 is a perspective view of an anastomotic ring applier device.
Figure 2:
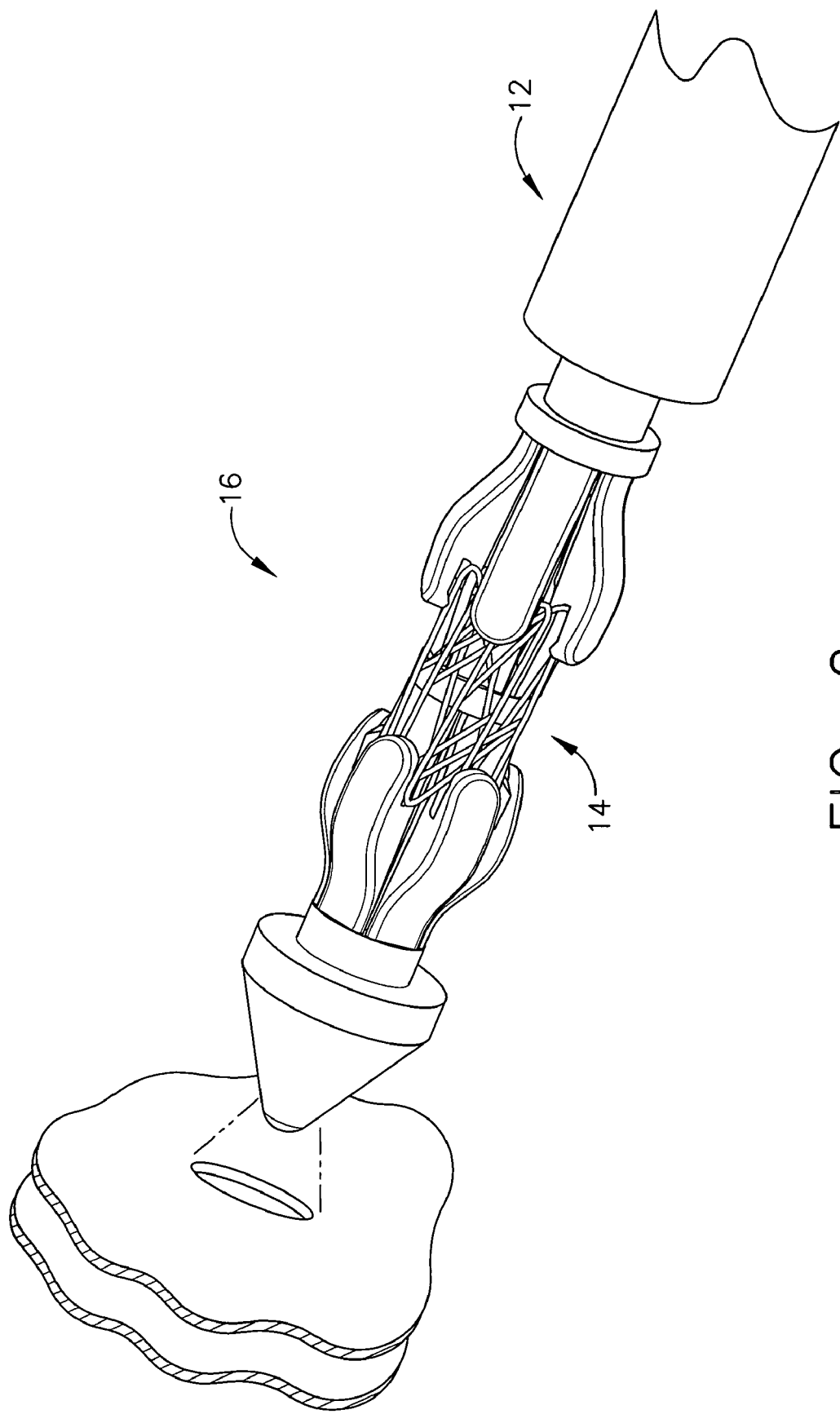
FIG. 2 is a partial perspective view of the distal portion of an anastomotic ring applier device holding an anastomotic ring in an unactuated position.
Figure 3:
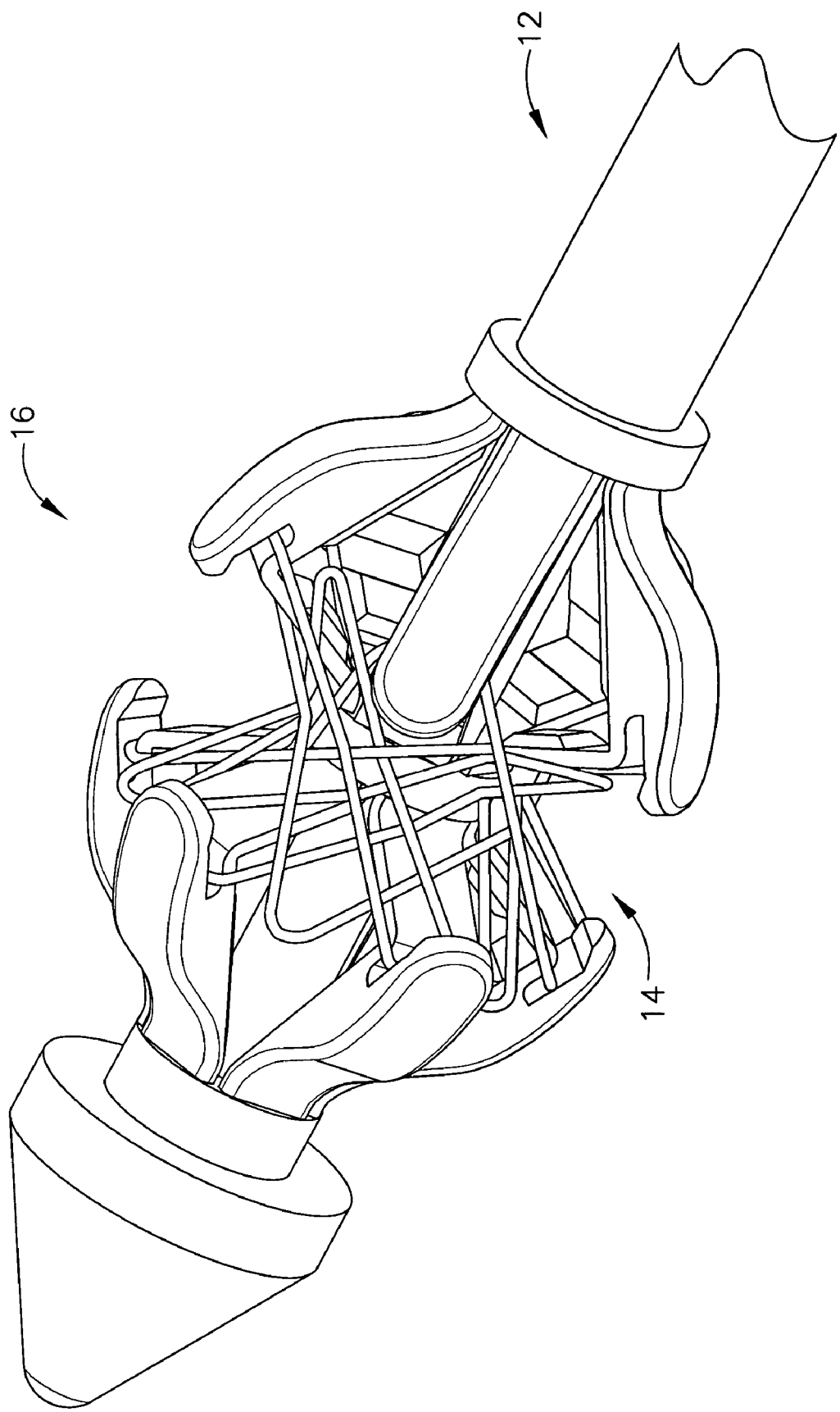
FIG. 3 is a partial perspective view of the distal portion of the device of FIG. 2 holding an anastomotic ring in the actuated position.
Figure 4:
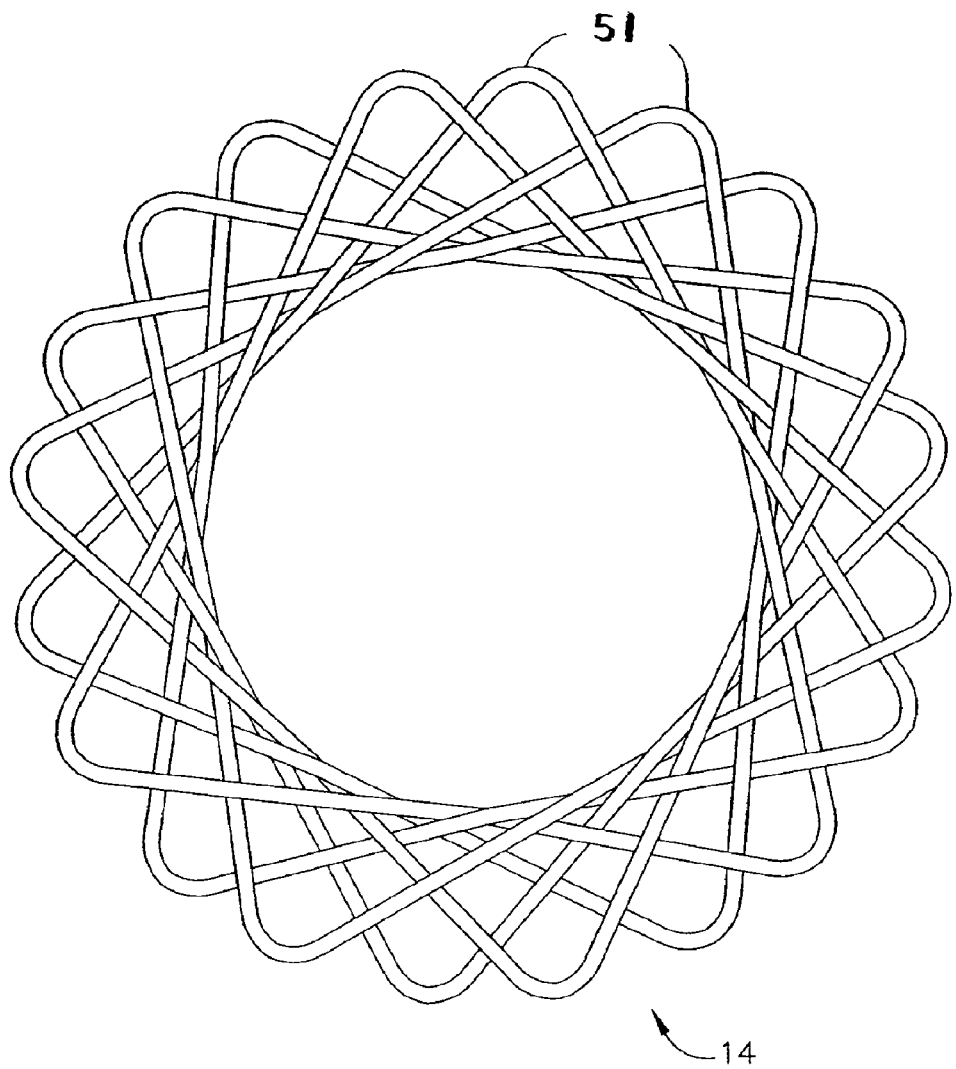
FIG. 4 is a frontal view of an actuated anastomotic ring.

Turning to the Drawings, wherein like numerals denote like components throughout the several views, FIG. 1 depicts an applier 10 that is operable to deploy and actuate an anastomotic ring device (not pictured in FIG. 1) from a generally cylindrical shape to one having properties of a hollow rivet, or ring, capable of forming an anastomotic attachment at an anastomosis target site, such as in a bariatric gastric bypass of a morbidly obese patient. FIG. 2 depicts another applier 12. It will be appreciated that appliers 10, 12 may be used in a variety of ways, including but not limited to laparoscopically or endoscopically. Applier 12 is shown in FIG. 2 with an anastomotic ring 14 on a deployment mechanism 16. In FIG. 2, anastomotic ring 14 is shown in the compressed, cylindrically-shaped position. In FIG. 3, deployment mechanism 16 of applier 12 has moved anastomotic ring 14 to the actuated, hollow rivet-shaped position. FIG. 4 is a close-up view of anastomotic ring 14 in the actuated position. Anastomotic ring 14 may comprise a shape memory effect (SME) material, such as nitinol by way of example only, that further assists in actuation to an engaging hollow rivet shape. Other suitable anastomotic ring 14 materials will be apparent to those of ordinary skill in the art. An exemplary anastomotic ring 14 is described in detail in U.S. Patent Application Publ. No. US 2003/0032967 to Park et al.

It will be appreciated that the terms "proximal" and "distal" are used herein with reference to a clinician gripping a handle of applier 10. It will be further appreciated that for convenience and clarity, spatial terms such as "right", "left", "vertical" and "horizontal" are used herein with respect to the drawings. However, surgical instruments are used in many orientations and positions, and these terms are not intended to be limiting and absolute. In addition, aspects of the invention have application to surgical procedures performed endoscopically and laparoscopically, as well as an open procedure or other procedures. Use herein of one of these or similar terms should not be construed to limit the present invention for use in only one category of surgical procedure.

Figure 5:
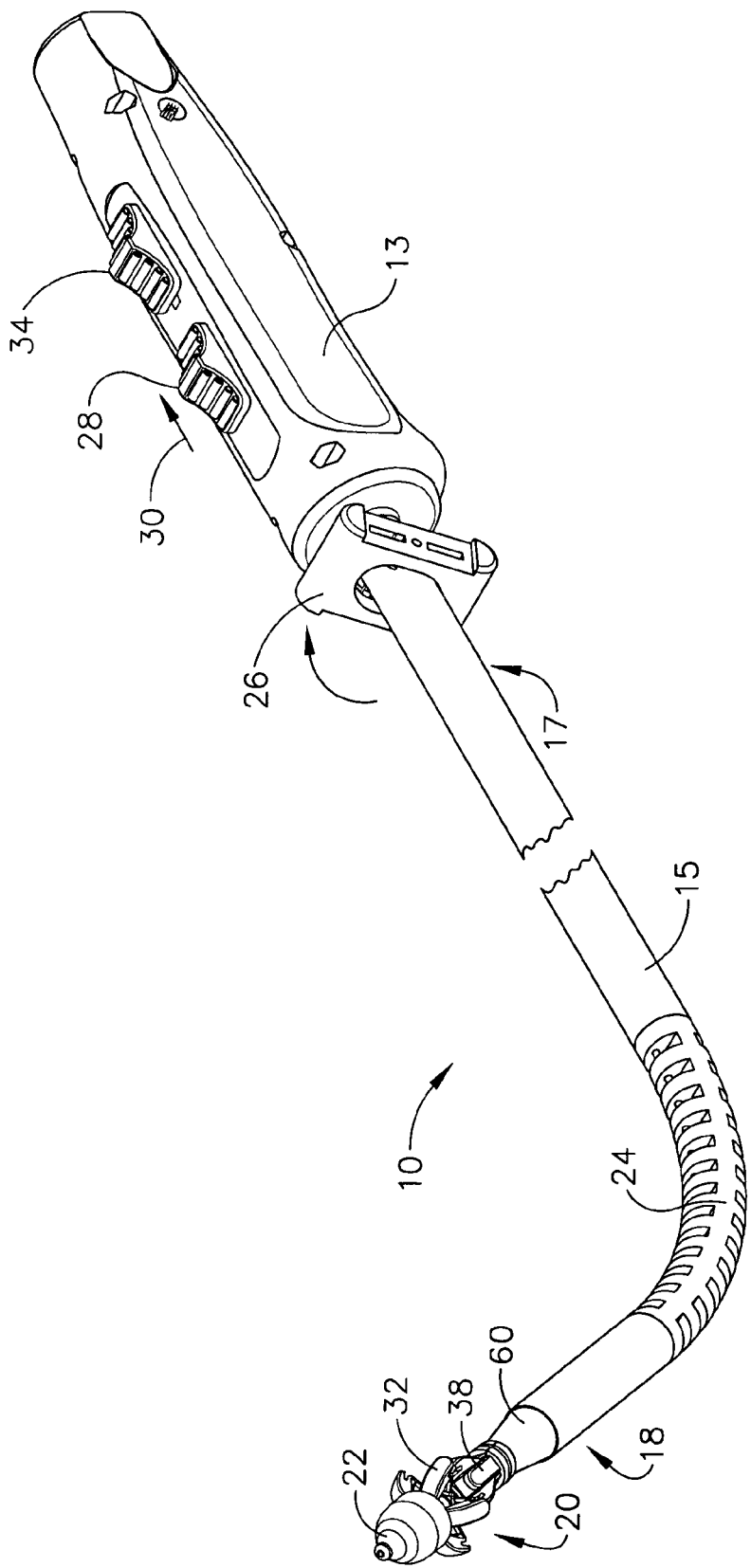
FIG. 5 is a perspective view of the device of FIG. 1, shown with the flexible joint articulated upwardly and the distal fingers actuated.
Figure 6:
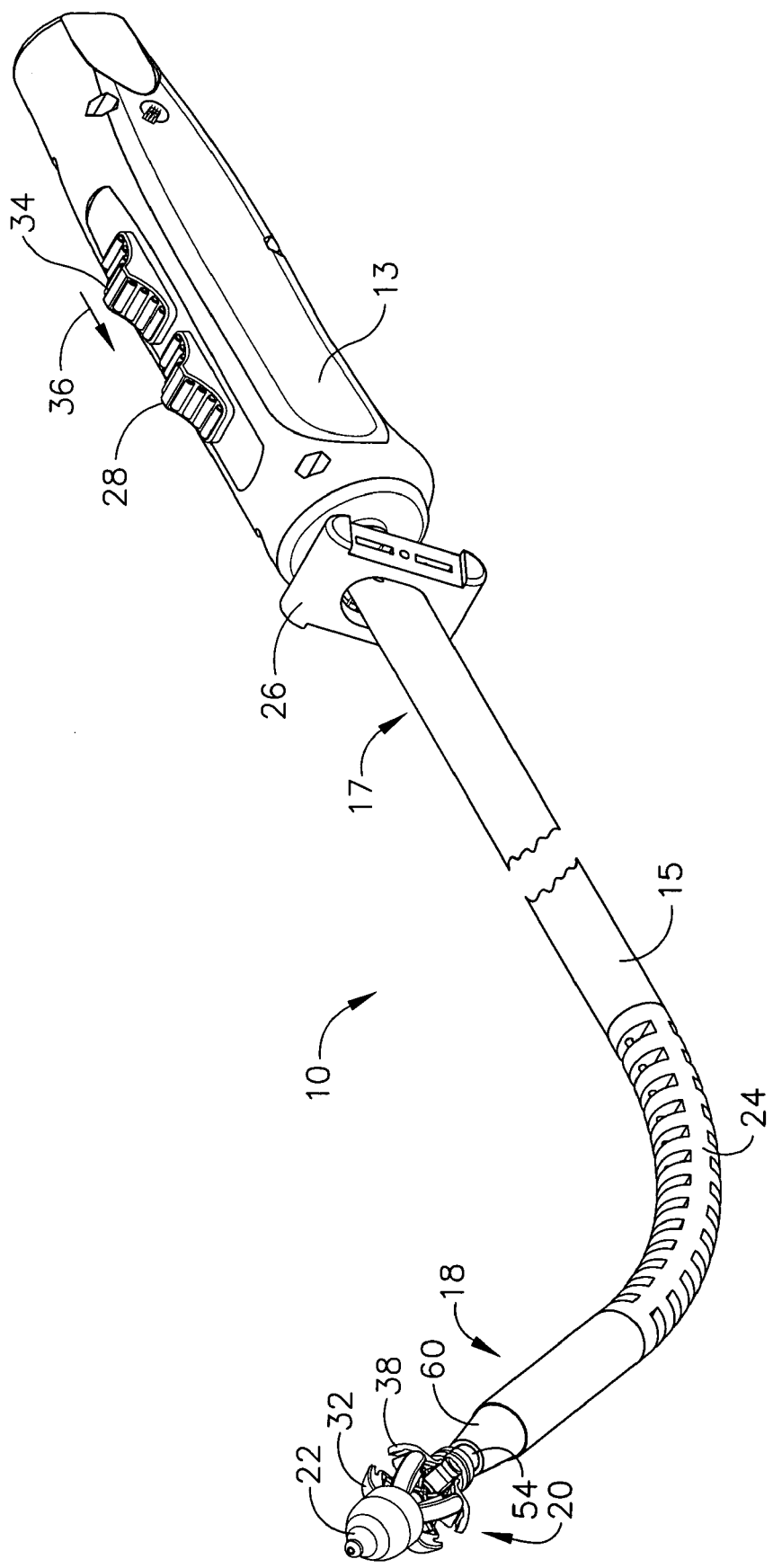
FIG. 6 is a perspective view of the device of FIG. 1, shown with the flexible joint articulated upwardly and the proximal and distal fingers actuated.

Referring to FIGS. 1, 5, and 6, applier 10 of the present example comprises a handle 13 and an elongated shaft 15 comprising a proximal portion 17 and a distal portion 18. Distal portion 18 comprises a ring deployment mechanism 20 and a tip 22. Tip 22 is attached to applier 10 by a hollow rod 23. Alternatively, or in addition, tip 22 may be attached to a distal portion of ring deployment mechanism 20. As further shown in FIG. 1, shaft 15 also comprises a flexible joint 24 that allows a surgeon to articulate distal portion 18 of shaft 15 and the ring deployment mechanism 20 contained thereon. While the illustrative embodiment of FIGS. 1, 5, and 6 depicts shaft 15 having only a single flexible joint 24, it will be appreciated that shaft 15 may comprise a plurality of flexible joints 24 in order to achieve greater articulation capabilities or for other purposes. Flexible joint 24 is shown as being ribbed, which may facilitate flexibility. Of course, flexible joint 24 may comprise a variety of alternative configurations.

In FIG. 5, distal portion 18 of shaft 15 is shown articulated in an upward direction by engagement of an actuator rocker 26, which is adapted to bend shaft 15 at flexible joint 24. Rocker 26 is pivotally attached to shaft 15, such that it may be actuated from a neutral position in either of two directions in order to articulate flexible joint 24 upward or downward in a single plane. Of course, actuator rocker 26 is merely illustrative, and a variety of alternative means, methods, or mechanisms may be used to effect articulation of shaft 15 at joint 24 or elsewhere. In addition, it will be appreciated that shaft 15 may be configured such that it is operable to articulate in more than one plane. Suitable alternative configurations for providing articulation of shaft 15, including but not limited to single or multi-plane articulation, will be apparent to those of ordinary skill in the art.

A first ring deployment actuator 28 is shown in FIG. 5 with an arrow 30 depicting motion from an unactuated position to an actuated position. Actuation of first actuator 28 may be adapted to actuate a plurality of distal fingers 32 of ring deployment mechanism 20, as shown in FIG. 5, to actuate a distal portion of an anastomotic ring. In addition, or in the alternative, first ring deployment actuator 28 may be operable to actuate a plurality of proximal fingers 38.

In FIG. 6, a second ring deployment actuator 34 is shown with an arrow 36 depicting motion from an unactuated position to an actuated position. Actuation of second actuator 34 may be adapted to actuate a plurality of proximal fingers 38 of ring deployment mechanism 20, as shown in FIG. 6, to deploy a proximal portion of an anastomotic ring. In addition, or in the alternative, second ring deployment actuator 34 may be operable to actuate a plurality of distal fingers 32.

Those of ordinary skill in the art will appreciate that first and second ring deployment actuators 28, 34 are merely exemplary. Accordingly, a variety of alternative means, methods, or mechanisms may be used to actuate distal fingers 32 and/or proximal fingers 38.

Figure 7:
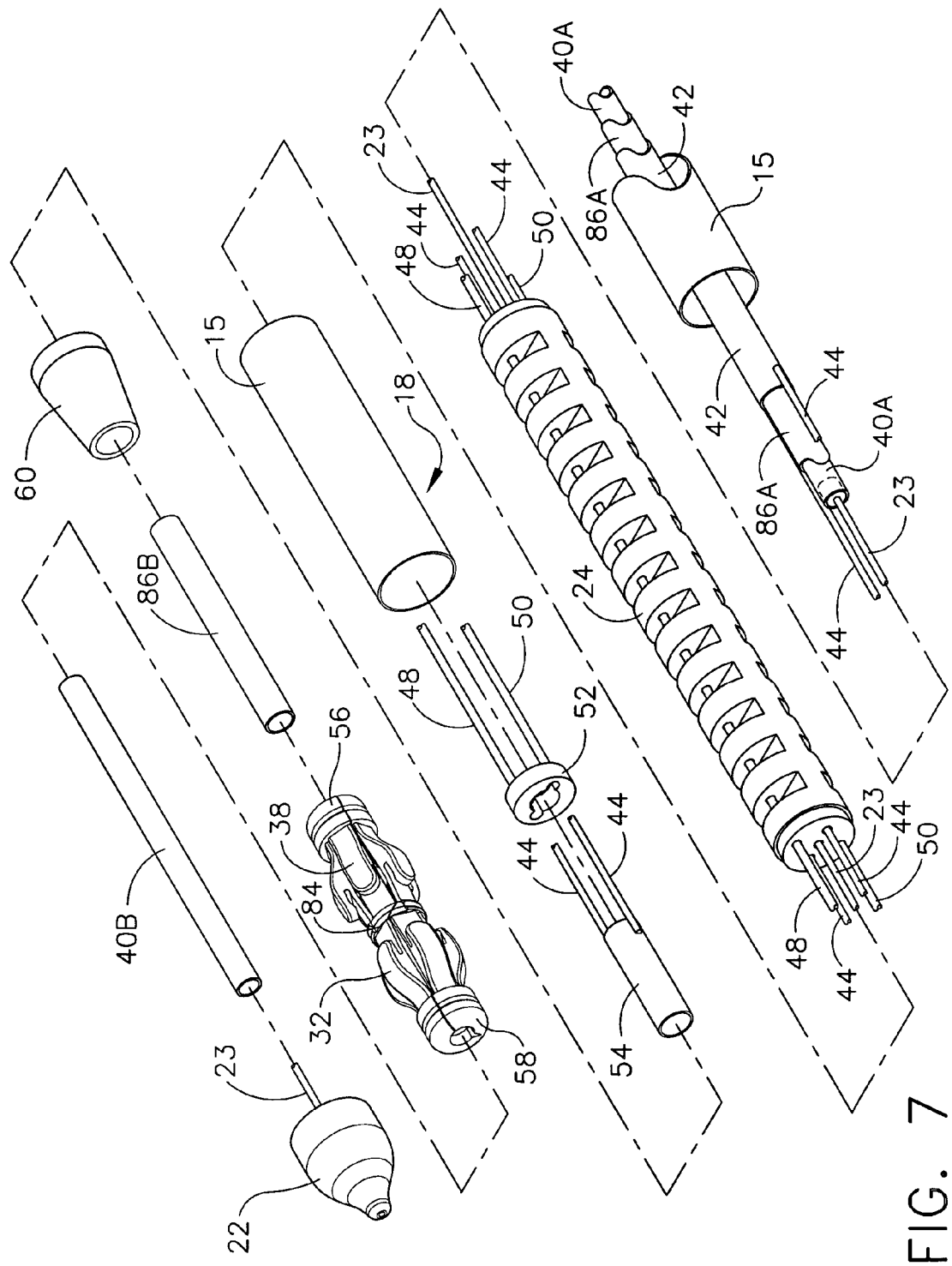
FIG. 7 is a perspective, exploded view of the anastomotic ring deployment mechanism of the device of FIG. 1.

Referring now to FIG. 7, distal portion 18 of shaft 15 is shown in an exploded view to depict one exemplary configuration operable to communicate motion to distal fingers 32 and proximal fingers 38 through flexible joint 24. Proximal of flexible joint 24, shaft 15 is pictured comprising a series of concentric tubes. An inner tube 40A extends longitudinally through a ground tube 86A. Ground tube 86A extends longitudinally through outer tube 42, and the distal end of ground tube 86A abuts the proximal end of flexible joint 24. In one embodiment, the distal end of ground tube 86A abuts the proximal end of flexible joint 24. In another embodiment, the distal end of ground tube 86A is fixed to the proximal end of flexible joint 24.

A pair of proximal cables 44 extend distally from outer tube 42, and are fixedly attached thereto. A distal cable 23 extends distally from inner tube 40A, and is fixedly attached thereto. Distal cable 23 and proximal cables 44 extend through the neutral plane of flexible joint 24. In this embodiment, the orientation of distal cable 23 and proximal cables 44 relative to one another is not changed by articulation of flexible joint 24. Those of ordinary skill in the art will appreciate that a variety of alternative configurations may be used, including but not limited to alternatives to tubes 40A, 86A, 42, and/or cables 44, 23.

Push/pull cables 48, 50 pass through the articulating plane of flexible joint 24. Push/pull cables 48, 50 terminate in an anchor member 52, and are fixedly attached thereto. In one embodiment, anchor member 52 abuts the distal end of flexible joint 24. In another embodiment, anchor member 52 is fixed to the distal end of flexible joint 24. Other suitable configurations will be apparent to those of ordinary skill in the art.

Proximal cables 44 extend from the distal end of flexible joint 24, pass through anchor member 52, and fixedly connect to a proximal tube 54. The distal end of proximal tube 54 fixedly connects to a proximal ring 56, which is attached to the base of proximal fingers 38.

As shown in FIGS. 7, 9, and 10, distal cable 23 extends from the distal end of flexible joint 24, passes through anchor member 52, and rigidly connects to tip 22. Tip 22 is connected to a distal ring 58, which is attached to the base of distal fingers 32. In addition, inner tube 40B is connected to distal ring 58, and is slidably disposed within ground tube 86B. It will be appreciated that distal cable 23 may be rigidly connected to inner tube 40B in addition to or as an alternative to being attached to tip 22. Of course, if distal cable 23 is rigidly connected to inner tube 40B, distal cable 23 need not fully extend to tip 22. Still other alternative configurations will be apparent to those of ordinary skill in the art.

Figure 12:
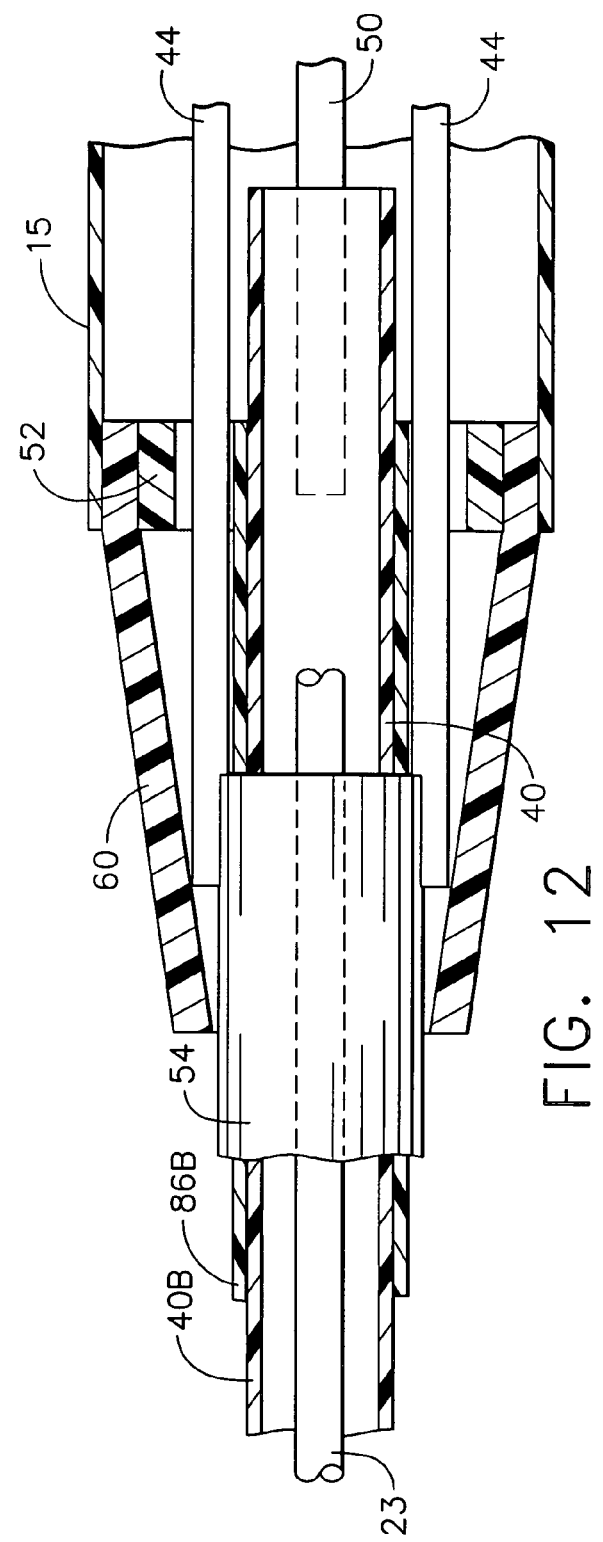
FIG. 12 is a partial cross-sectional view taken along Plane 12 of the instrument of FIG. 10.

Applier 10 further comprises a transition member 60 (FIG. 12) to transition between shaft 15 and the smaller diameter of ring deployment mechanism 20. In one embodiment, anchor member 52 is fixed to transition member 60. While transition member 60 is shown as having a generally frustoconical configuration, it will be appreciated that transition member may comprise a variety of alternative configurations.

In an alternative embodiment, an insufflation passage extends longitudinally from an air port (not pictured) on handle 13 through applier 10 to tip 22. It will be appreciated that distal cable 23 may be substituted with a hollow member that is configured to serve dual functions of distal cable 23 and insufflation passage, by way of example only. Alternatively, the insufflation passage may be in coaxial alignment with distal cable 23, or positioned adjacent distal cable 23. Similarly, more than one distal cable 23 may be used. Still other suitable configurations for providing an insufflation passage and/or varying distal cable 23 will be apparent to those of ordinary skill in the art.

Figure 8:
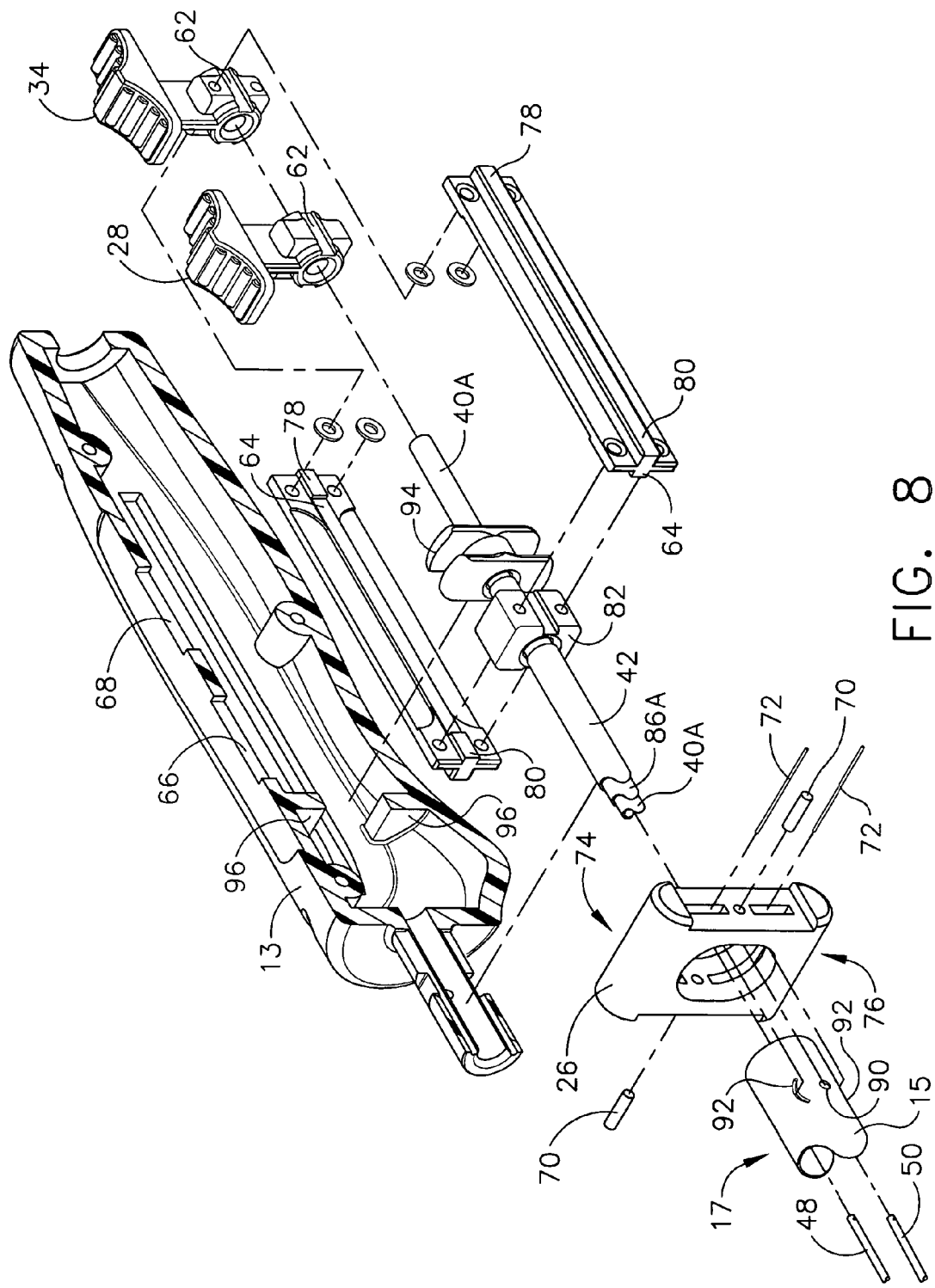
FIG. 8 is a perspective, cross-sectional exploded view of a proximal portion of the device of FIG. 1 with a left housing half omitted.
Figure 15:
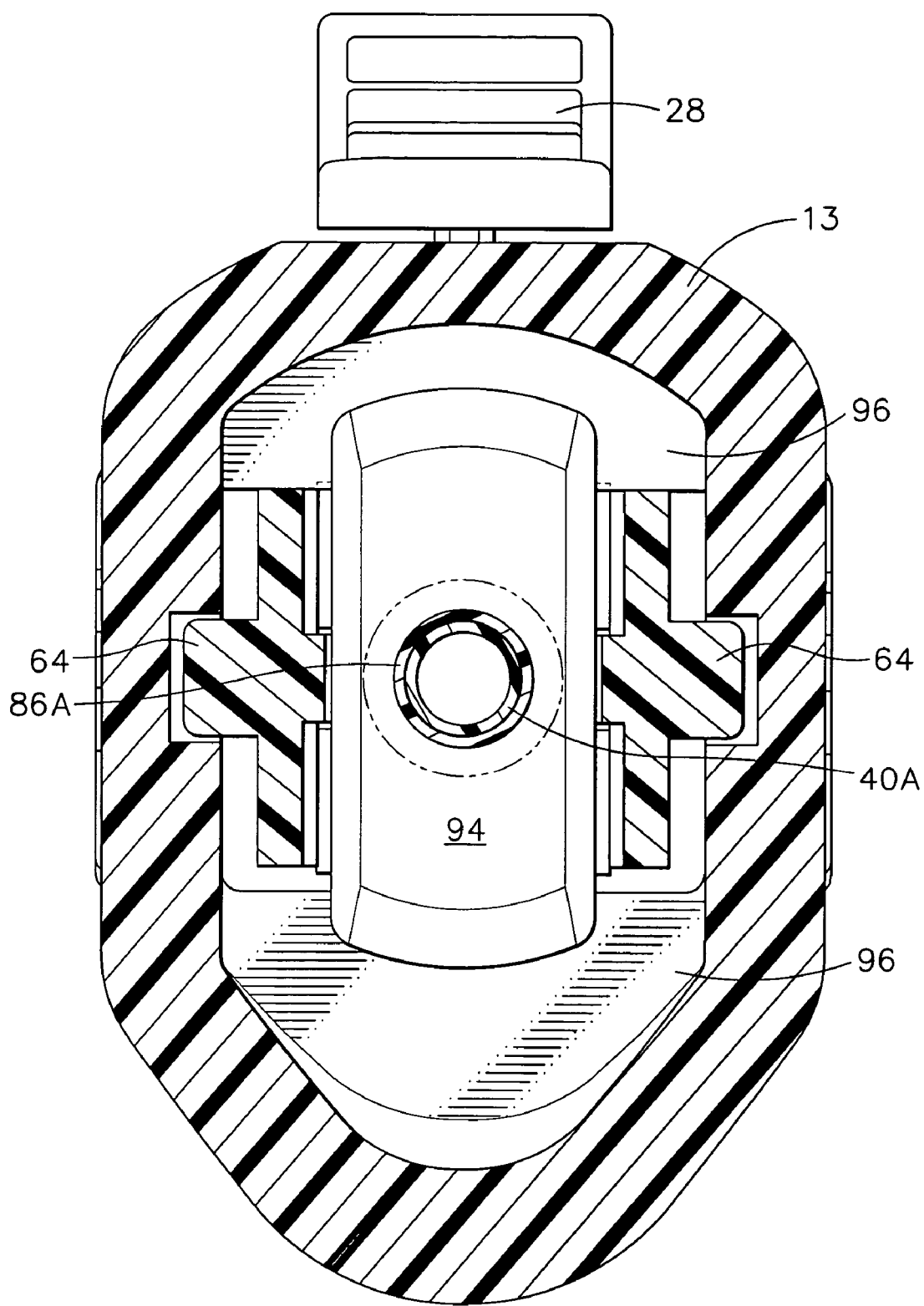
FIG. 15 is a cross-sectional view taken along Plane 15 of the device of FIG. 13.

Referring now to FIG. 8, proximal portion 17 of shaft 15 and handle 13 are shown in an exploded view, omitting the right half of shaft 15, in order to depict one configuration operable to communicate motion to distal fingers 32, proximal fingers 38, and flexible joint 24. First and second ring deployment actuators 28, 34 each comprise a pair of grooves 62 that are configured to slide on a track 64 of handle 13 (FIG. 15). The longitudinal range of first actuator 28 may limited by the width of a slot 66, while the range of second actuator 34 may be limited by the width of a slot 68.

Figure 14:
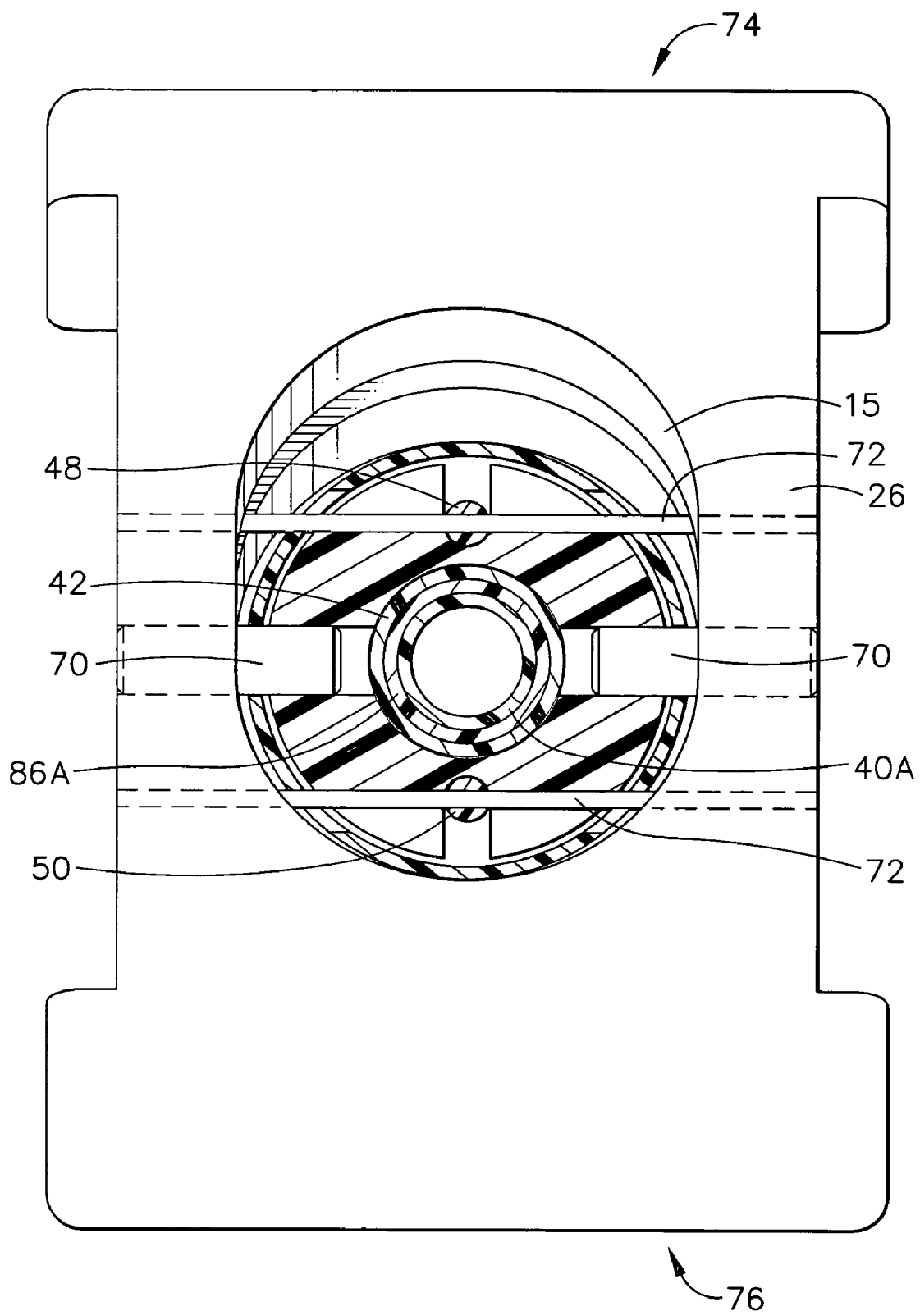
FIG. 14 is a cross-sectional view taken along Plane 14 of the device of FIG. 13.

Rocker 26 is pivotally attached to proximal portion 17 of shaft 15 by pins 70. Proximal portion 17 of shaft 15 includes a pair of openings 90 configured to receive pins 70. Push/pull cables 48, 50 are each connected to shaft 15 and rocker 26 by pins 72 (FIG. 14). Proximal portion 17 of shaft 15 includes a pair of radiused slots 92 configured to receive pins 72. As shown in FIGS. 8 and 14, rocker 26 comprises an upper portion 74 and a lower portion 76. Push/pull cable 48 corresponds to upper portion 74 of rocker 26, while push/pull cable 50 corresponds to lower portion 76. In this embodiment, push/pull cables 48, 50 are spaced apart in the plane of articulation of flexible joint 24, such that actuation of rocker 26 in a first direction causes push/pull cable 48 to move proximally and push/pull cable 50 to move distally, causing flexible joint 24 to bend upwardly, as shown in FIGS. 5 and 6. Similarly, actuation of rocker 26 in a second direction causes push/pull cable 48 to move distally and push/pull cable 50 to move proximally, causing flexible joint 24 to bend downwardly.

Of course, any suitable substitute for or supplement to rocker 26 may be used. By way of example only, rocker 26 may be substituted by a knob or other member configured to move in an angular direction positioned in handle 13 or elsewhere. Where a knob or similar member is used as a substitute for rocker 26, push/pull cables 48, 50 may be connected thereto, such that rotation of the knob or similar member causes articulation at articulation joint 24. Still other suitable alternative configurations will be apparent to those of ordinary skill in the art.

In the present example, first ring deployment actuator 28 is operable to control distal fingers 32, and second ring deployment actuator 34 is operable to control proximal fingers 38. Second actuator 34 is fixedly attached to a proximal portion 78 of track 64. Track 64 is slideable within handle 13. A distal portion 80 of track 64 is fixedly attached to a slider 82. Slider 82 is fixedly connected to outer tube 42. Longitudinal motion of second actuator 34 thereby causes corresponding longitudinal motion of track 64, slider 82, and outer tube 42. As described above with reference to FIG. 7, outer tube 42 is connected to proximal cables 44, and is thereby operable to communicate motion to proximal fingers 38 through flexible joint 24.

First actuator 28 is fixedly connected to inner tube 40A. Inner tube 40A extends longitudinally through ground tube 86A, which extends longitudinally through outer tube 42. Inner tube 40A is operable to communicate motion to distal fingers 32. In this manner, first actuator 28 is operable to control distal fingers 32, and second actuator 34 is operable to control proximal fingers 38. It should be noted that although first actuator 28 is adapted to slide on track 64, it is not statically attached to it. Therefore, longitudinal movement of track 64 through motion of second actuator 34 will not cause any movement of first actuator 28.

In the present example, the proximal end of ground tube 86A is fixedly attached to anchor member 94. Anchor member 94 is configured to engage with bosses 96 in handle 13, thereby preventing relative motion between handle 13 and ground tube 86A.

Those of ordinary skill in the art will appreciate that a variety of alternative components and/or configurations may be used to effect actuation of distal fingers 32 and/or proximal fingers 38. By way of example only, one alternative configuration may include configuring second actuator 34 to be operable to control actuation of distal fingers 32, and configuring first actuator 28 to be operable to control actuation of proximal fingers 38. Other suitable variations will be apparent to those of ordinary skill in the art.

FIG. 9 shows ring deployment mechanism 20 in the unactuated position. FIG. 10 shows ring deployment mechanism 20 in the actuated position. FIG. 10 depicts how proximal motion of distal ring 58 (caused by proximal motion of distal cable and/or inner tube 40B) results in distal ring 58 moving toward a stationary mid-ring 84 of ring deployment mechanism 20. Mid-ring 84 is fixedly attached to ground tube 86B. Ground tube 86B is fixedly attached to anchor member 52. Accordingly, in the present example, there is no relative movement between ground tube 86B and shaft 15 or mid-ring 84 during operation of applier 10. Distal fingers 32 are in a double-hinged relationship with mid-ring 84, such that proximal motion of distal ring 58 causes the tips of distal fingers 32 to articulate outwardly and deploy a distal portion of an anastomotic ring. Distal fingers 32 are configured to hold the distal portion of the anastomotic ring by engaging petals 51 prior to and during deployment of the anastomotic ring, and release petals 51 upon deployment of the anastomotic ring.

Similarly, as shown in FIG. 10, proximal tube 54 is fixedly connected to proximal ring 56, such that distal motion of proximal tube 54 causes proximal ring 56 to move toward mid-ring 84. Proximal fingers 38 and mid-ring 84 are in a double-hinged relationship, such that distal motion of proximal ring 56 causes the tips of proximal fingers 38 to articulate outwardly and deploy a proximal portion of an anastomotic ring. Proximal fingers 38 are configured to hold the proximal portion of the anastomotic ring by engaging petals 51 prior to and during deployment of the anastomotic ring, and release petals 51 upon deployment of the anastomotic ring.

While fingers 32, 38 are shown and described as articulating outwardly via a double-hinged relationship with mid-ring 84, it will be appreciated that a variety of other configurations for ring deployment mechanism 20 may be used to effect deployment of an anastomotic ring. Such alternate configurations will be apparent to those of ordinary skill in the art.

Figure 11:
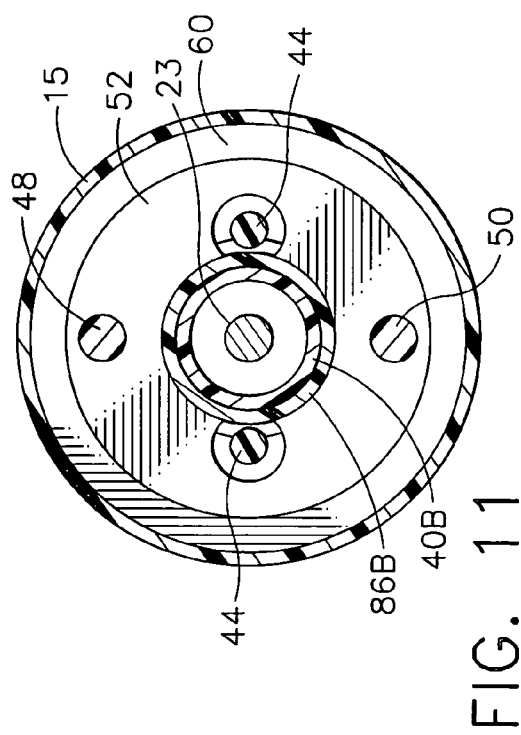
FIG. 11 is a cross-sectional view taken along Plane 11 of the device of FIG. 10.

FIG. 11 shows a frontal cross-section of flexible joint 24. Articulation push/pull cables 48, 50 are shown aligned in the articulating plane, allowing engagement of rocker 26 to bend flexible joint 24 in the articulating plane. Proximal cables 44 are also shown flanking inner tube 40, through which distal cable 23 passes.

Figure 13:
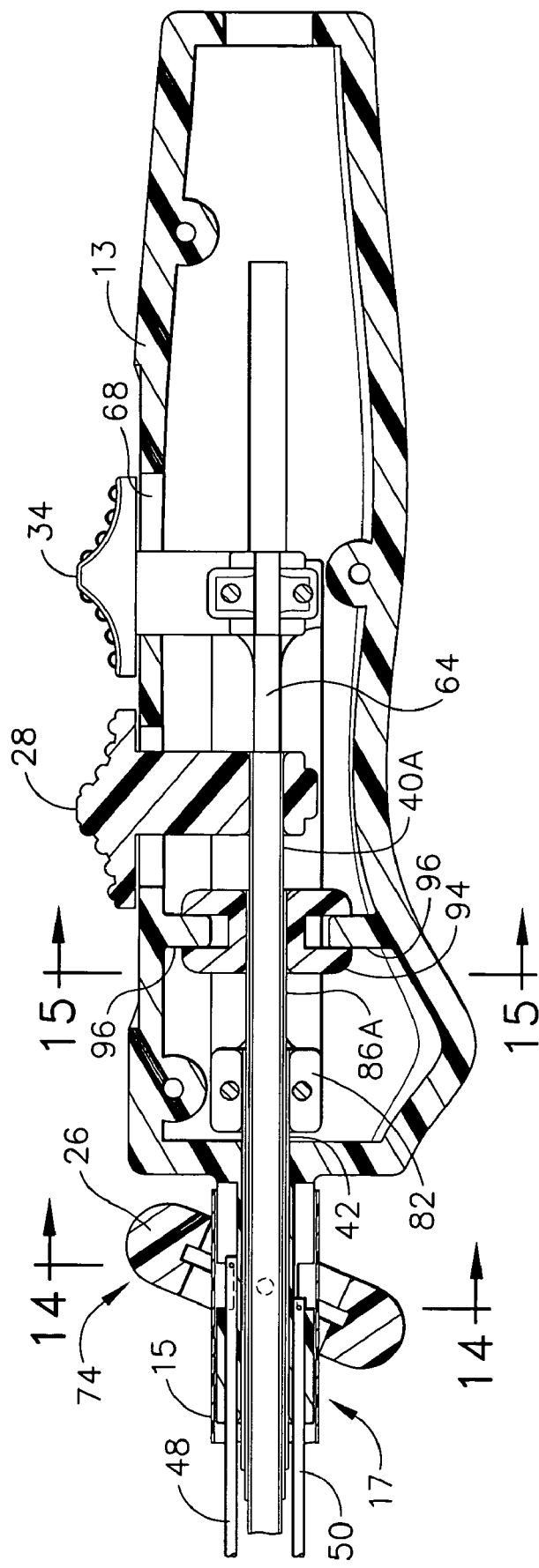
FIG. 13 is a is a partial cross-sectional view of a proximal portion of the device of FIG. 1 in the actuated position.

FIG. 13 shows a cross-section of proximal portion 17 of shaft 15 and handle 13. In FIG. 13, second actuator 34 is shown pushed to the distal end of slot 68, forcing slider 82 and outer tube 42 distally, causing proximal fingers 38 to actuate outwardly, as shown in FIG. 10. FIG. 13 also depicts upper portion 74 of rocker 26 actuated proximally. As pictured, this causes push/pull cable 48 to move proximally and push/pull cable 50 to move distally, causing flexible joint 24 to bend upwardly, as shown in FIG. 5.

Having shown and described various embodiments and concepts of the invention, further adaptations of the methods and systems described herein can be accomplished by appropriate modifications by one of ordinary skill in the art without departing from the scope of the invention. Several of such potential alternatives, modifications, and variations have been mentioned, and others will be apparent to those skilled in the art in light of the foregoing teachings. Accordingly, the invention is intended to embrace all such alternatives, modifications and variations as may fall within the spirit and scope of the appended claims and is understood not to be limited to the details of structure and operation shown and described in the specification and drawings. Additional advantages may readily appear to those skilled in the art.

What is claimed is:

1. A surgical instrument operable to implant an anastomotic ring, wherein the anastomotic ring comprises a plurality of petals, the instrument comprising:
    a handle comprising a first actuator and a second actuator;
    a ring deployment mechanism configured to receive and deploy the anastomotic ring, wherein said ring deployment mechanism defines a longitudinal axis, wherein said ring deployment mechanism comprises:
        (i) a proximal ring situated about said longitudinal axis,
        (ii) a first plurality of fingers, wherein each finger of the first plurality of fingers comprises a proximal segment and a distal segment, wherein the proximal segment of each finger of the first plurality of fingers is hingedly connected to the corresponding distal segment of the same finger of the first plurality of fingers at a corresponding finger joint, wherein the proximal segment of each finger of the first plurality of fingers is further hingedly connected to said proximal ring,
        (iii) a distal ring situated about said longitudinal axis,
        (iv) a second plurality of fingers, wherein each finger of the second plurality of fingers comprises a proximal segment and a distal segment, wherein the proximal segment of each finger of the second plurality of fingers is hingedly connected to the corresponding distal segment of the same finger of the second plurality of fingers at a corresponding finger joint, wherein the distal segment of each finger of the second plurality of fingers is further hingedly connected to said distal ring, and
        (v) a middle ring positioned in between said proximal ring and said distal ring, wherein the distal segment of each finger of the first plurality of fingers is further hingedly connected to the middle ring, wherein the proximal segment of each finger of the second plurality of fingers is further hingedly connected to the middle ring, wherein the middle ring longitudinally separates the distal segments of the first plurality of fingers from the proximal segments of the second plurality of fingers;
    an elongate shaft connecting the handle to the ring deployment mechanism, wherein the elongate shaft is configured to transfer actuating force from the handle to the ring deployment mechanism, wherein the elongate shaft comprises:
        (i) a flexible joint that is configured to allow the elongate shaft to articulate,
        (ii) an outer tube operably connected to said proximal ring, and
        (iii) an inner tube fixedly connected to said second actuator and operably connected to said distal ring;
    a joint actuator operable to effect articulation of the elongate shaft at the flexible joint;
    wherein the finger joints of each of said plurality of fingers are radially movable inwardly and outwardly relative to said longitudinal axis;
    wherein each finger of said plurality of fingers is configured to alternately assume a retracted position and an extended position relative to said longitudinal axis;
    wherein each finger of said plurality of fingers is configured to engage and radially inwardly restrain a respective petal of said plurality of petals on a first portion of the anastomotic ring when in the plurality of fingers are in said retracted position;
    wherein each finger of said plurality of fingers is further operable to release the respective petal of said plurality of petals when the plurality of fingers are moved to said extended position;
    wherein movement of said first actuator in a proximal direction causes said proximal ring to travel towards said middle ring and said first plurality of fingers to actuate outwardly by flexing at the corresponding finger joints;
    wherein movement of said second actuator in a distal direction causes said distal ring to travel towards said middle ring and said second plurality of fingers to actuate outwardly by flexing at the corresponding finger joints;
    wherein the first plurality of fingers are moveable independently relative to the second plurality of fingers.

2. The surgical instrument of claim 1, wherein the joint actuator is configured to move from a neutral position to a first, activated position to bend the flexible joint in a first direction.

3. The surgical instrument of claim 2, wherein the joint actuator is configured to move from a neutral position to a second, activated position to bend the flexible joint in a second direction.

4. The surgical instrument of claim 1, further comprising a first actuation cable configured to communicate a first actuation force from the first actuator through the flexible joint to the first plurality of fingers, wherein said first actuation cable is positioned between said outer tube and said proximal ring.

5. The surgical instrument of claim 1, further comprising a second actuation cable configured to communicate a second actuation force from the second actuator through the flexible joint to the second plurality of fingers, wherein said second actuation cable is positioned between said inner tube and said distal ring.

6. The surgical instrument of claim 1, wherein the flexible joint comprises a ribbed member.

7. A surgical instrument operable to implant an anastomotic ring, wherein the anastomotic ring comprises a plurality of petals, the instrument comprising:
   a handle comprising:
   (i) a first actuator, and
   (ii) a second actuator;
   a ring deployment mechanism configured to receive and deploy the anastomotic ring, wherein said ring deployment mechanism defines a longitudinal axis, wherein said ring deployment mechanism comprises:
   (i) a proximal ring situated about said longitudinal axis,
   (ii) a first plurality of fingers, wherein each finger of the first plurality of fingers comprises a proximal segment and a distal segment, wherein the distal segment of each finger of the first plurality of fingers is hingedly connected to the corresponding proximal segment of the same finger at a corresponding finger joint, wherein the proximal segment of each finger of the first plurality of fingers is further hingedly connected to said proximal ring, wherein each proximal segment of each finger of the first plurality of fingers further comprises an internal gripping slot adjacent to the corresponding finger joint of the corresponding finger of the first plurality of fingers, wherein each gripping slot of the first plurality of fingers is configured to receive a respective petal of the anastomotic ring,
   (iii) a distal ring situated about said longitudinal axis,
   (iv) a second plurality of fingers, wherein each finger of the second plurality of fingers comprises a proximal segment and a distal segment, wherein the distal segment of each finger of the second plurality of fingers is hingedly connected to the corresponding proximal segment of the same finger at a corresponding finger joint, wherein the distal segment of each finger of the second plurality of fingers is further hingedly connected to said distal ring, wherein each distal segment of each finger of second first plurality of fingers further comprises an internal gripping slot adjacent to the corresponding finger joint of the corresponding finger of the second plurality of fingers, wherein each gripping slot of the second plurality of fingers is configured to receive a respective petal of the anastomotic ring, and
   (v) a mid-ring positioned in between said proximal ring and said distal ring, wherein the distal segment of each finger of the first plurality of fingers is further hingedly connected to the mid-ring, wherein the proximal segment of each finger of the second plurality of fingers is further hingedly connected to the mid-ring, wherein the mid-ring longitudinally separates the distal segments of the first plurality of fingers from the proximal segments of the second plurality of fingers;
   an elongate shaft connecting the handle to the ring deployment mechanism, wherein the elongate shaft includes a flexible joint that is configured to allow the elongate shaft to articulate;
   at least one push/pull cable operable to articulate the flexible joint;
   an inner tube fixably connected to said second actuator, and positioned within said handle;
   an outer tube positioned within said handle;
   a distal tube fixably connected to said distal ring;
   a proximal tube fixably connected to said proximal ring;
   a pair of proximal cables fixably attached to said outer tube and said proximal tube, wherein said proximal cables extend distally from said outer tube to said proximal tube; and
   a distal cable fixably attached to said inner tube and said distal tube, wherein said distal cable extends distally from said inner tube to said distal tube;
   wherein each of said plurality of fingers has a portion that is radially movable relative to said longitudinal axis;
   wherein each finger of said plurality of fingers is configured to alternately assume a retracted position and an extended position relative to said longitudinal axis;
   wherein each finger of said plurality of fingers is configured to engage and radially inwardly restrain a respective petal of said plurality of petals on a first portion of the anastomotic ring when in the plurality of fingers are in said retracted position;
   wherein each finger of said plurality of fingers is further operable to release the respective petal of said plurality of petals when the plurality of fingers are moved to said extended position;
   wherein movement of said first actuator in a proximal direction causes said proximal ring to travel towards said mid-ring and said second plurality of fingers to actuate outwardly by flexing at the corresponding finger joints;
   wherein movement of said second actuator in a distal direction causes said distal ring to travel towards said mid-ring and said first plurality of fingers to actuate outwardly by flexing at the corresponding finger joints.

8. A surgical instrument operable to implant an anastomotic ring, wherein the anastomotic ring comprises a plurality of petals, the instrument comprising:
   an actuating member configured to receive an anastomotic ring, wherein the actuating member is moveable between a cylindrical, unactuated position and a hollow rivet forming actuated position in response to at least one compressive actuating force, wherein the actuating member defines a longitudinal axis, wherein the actuating member is configured to alternately hold the petals of the anastomotic ring in radially retracted positions relative to the longitudinal axis and release the petals to radially extended positions relative to the longitudinal axis, wherein the actuating member further comprises:
   (i) a proximal base member positioned about the longitudinal axis, wherein the proximal base member is longitudinally movable about the longitudinal axis,
   (ii) a middle base member located at a fixed longitudinal position about the longitudinal axis,
   (iii) a distal base member positioned about the longitudinal axis, wherein the distal base member is longitudinally movable about the longitudinal axis,
   (iv) at least one proximal finger, wherein the at least one proximal finger comprises a distal segment and a proximal segment, wherein the distal segment of the at least one proximal finger is hingedly connected to the proximal segment of the at least one proximal finger at a corresponding finger joint, wherein the proximal segment of the at least one proximal finger is further hingedly connected to the proximal base member, wherein the distal segment of the at least one proximal finger is further hingedly connected to the middle base member, wherein the proximal segment of the at least one proximal finger further comprises an internal gripping slot adjacent to the finger joint of the at least one proximal finger, wherein the gripping slot is configured to receive a petal of the anastomotic ring, wherein the gripping slot opens in a longitudinal direction substantially parallel to the longitudinal axis when the actuating member is in an unactuated position, and (v) at least one distal finger, wherein the at least one distal finger comprises a distal segment and a proximal segment, wherein the distal segment of the at least one distal finger is hingedly connected to the proximal segment of the at least one distal finger at a corresponding finger joint, wherein the proximal segment of the at least one distal finger is further hingedly connected to the middle base member, wherein the distal segment of the at least one distal finger is further hingedly connected to the distal base member, wherein the distal segment of the at least one distal finger further comprises an internal gripping slot adjacent to the finger joint of the at least one distal finger, wherein the gripping slot is configured to receive a petal of the anastomotic ring, wherein the gripping slot opens in a longitudinal direction substantially parallel to the longitudinal axis when the actuating member is in an unactuated position;

a handle including an actuation mechanism operable to produce the at least one compressive actuating force wherein the actuation mechanism comprises:

(i) a first actuator, and (ii) a second actuator;

an elongate shaft connecting the handle to the actuating member and operatively configured to transfer the at least one compressive actuating force from the handle to the actuating member, wherein the shaft comprises a flexible joint;

a joint actuator operable to articulate the flexible joint, wherein the joint actuator comprises a rocker pivotally attached to the shaft by at least one pin, wherein the rocker comprises an upper portion and a lower portion;

a pair of push/pull cables aligned in an articulating plane connecting the joint actuator to the flexible joint, wherein a first of the pair of push/pull cables is connected to the upper portion of the rocker, wherein a second of the push/pull cables is connected to the lower portion of the rocker;

an inner tube fixably connected to said second actuator, and positioned within said handle;

an outer tube positioned within said handle;

a distal tube fixably connected to said distal base member;

a proximal tube fixably connected to said proximal base member;

a pair of proximal cables fixably attached to said outer tube and said proximal tube, wherein said proximal cables extend distally from said outer tube to said proximal tube; and a distal cable fixably attached to said inner tube and said distal tube, wherein said distal cable extends distally from said inner tube to said distal tube;

wherein movement of said first actuator in a proximal direction causes said proximal base member to travel towards said middle base member and said at least one proximal finger to actuate outwardly by flexing at the corresponding finger joint;

wherein movement of said second actuator in a distal direction causes said distal base member to travel towards said middle base member and said at least one distal finger to actuate outwardly by flexing at the corresponding finger joint.

* * * * *

UNITED STATES PATENT AND TRADEMARK OFFICE
CERTIFICATE OF CORRECTION

| | | |
|---|---|---|
| PATENT NO. | : 7,645,287 B2 | Page 1 of 1 |
| APPLICATION NO. | : 11/121345 | |
| DATED | : January 12, 2010 | |
| INVENTOR(S) | : Ortiz | |

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 459 days Delete the phrase "by 459 days" and insert -- by 562 days --

Signed and Sealed this

Thirteenth Day of April, 2010

David J. Kappos
*Director of the United States Patent and Trademark Office*